United States Patent [19]
Rubenstein et al.

[11] Patent Number: 5,976,499
[45] Date of Patent: Nov. 2, 1999

[54] MACROSCOPIC SWEAT TEST FOR CYSTIC FIBROSIS

[75] Inventors: Ronald Craig Rubenstein, Ardmore, Pa.; Pamela Leslie Zeitlin, Baltimore, Md.

[73] Assignee: Johns Hopkins University, Baltimore, Md.

[21] Appl. No.: 09/148,122

[22] Filed: Sep. 4, 1998

[51] Int. Cl.⁶ .......................... A61K 49/00; G01N 31/00; G01N 33/48
[52] U.S. Cl. .......................... 424/9.1; 424/1.11; 424/9.2; 206/223; 206/569; 206/570
[58] Field of Search .................................. 424/1.11, 9.1, 424/9.2; 206/223, 569, 570; 546/131, 91; 514/304, 291; 544/267

[56] References Cited

U.S. PATENT DOCUMENTS

| | | | |
|---|---|---|---|
| 3,552,929 | 1/1971 | Fields et al. | 128/2 |
| 4,195,641 | 4/1980 | Joines et al. | 128/634 |
| 4,386,062 | 5/1983 | Beadle | 424/9 |
| 4,444,193 | 4/1984 | Fogt et al. | 128/632 |
| 4,457,748 | 7/1984 | Lattin et al. | 604/20 |
| 4,756,314 | 7/1988 | Eckenhoff et al. | 128/760 |
| 4,846,182 | 7/1989 | Fogt et al. | 128/632 |
| 5,438,984 | 8/1995 | Schoendorfer | 128/632 |
| 5,465,713 | 11/1995 | Schoendorfer | 128/632 |

OTHER PUBLICATIONS

Sato, K. et al, (1984), *J. Clin. Invest,* vol. 73, pp. 1763–1771.
Sato, K., et al., (1988), *J. Lab. Clin. Med.,* vol. 111, pp. 511–518.
Behm, J.K., et al., (1987), *Pedatric Research,* vol. 22, No. 3, pp. 271–276.

*Primary Examiner*—S. Mark Clardy
*Assistant Examiner*—Dameron Jones
*Attorney, Agent, or Firm*—Peter F. Corless; Cara Z. Lowen; Dike, Bronstein, Roberts & Cushman, LLP

[57] ABSTRACT

The present invention relates to methods of diagnosing CF comprising: stimulating sweat production via β-adrenergic pathway, by increasing cAMP production; collecting sweat into a sweat collection device; determining the sweat rate as a function of the weight of the sweat collected; correlating the sweat rate with the functional state of CFTR and/or presence or absence of CF. The invention also relates to methods of screening compounds for treatment of cystic fibrosis.

17 Claims, No Drawings

MACROSCOPIC SWEAT TEST FOR CYSTIC FIBROSIS

FIELD OF THE INVENTION

This invention relates to methods for discriminating between fully functional, partially functional and non-functional forms of the Cystic Fibrosis Transmembrane Conductance Regulator (CFTR). More particularly, this invention relates to a macroscopic cyclic-AMP (cAMP)-stimulated "sweat rate" test that will discriminate between fully functional, partially functional, and non-functional forms of CFTR.

BACKGROUND OF THE INVENTION

Cystic fibrosis (CF) is one of the most common genetic diseases among Caucasians and is a contributing factor in causing suffering among children and adults. CF affects the mucus-producing glands and other exocrine glands in the body. The gene encoding CFTR, the absence of function of which is responsible for causing CF, is located on chromosome 7q. Lack of CFTR function causes abnormal mucus production in the respiratory and gastrointestinal tracts and abnormal sweat gland function. Clinically, CF is characterized by chronic respiratory infections and obstructive lung disease, pancreatic gland insufficiency leading to an inability to digest fats, male infertility and abnormally high levels of electrolytes in the sweat.

CF is the most common lethal autosomal recessive disorder in the Caucasian population occurring in approximately 1 in 2,500 live births. Therefore, about 1 in 50 people is a carrier of CF. It is less common in other populations, occurring in approximately 1 in 18,000 African-Americans and about 1 in every 33,000 Asian-Americans. The median age of survival is 31. The life expectancy of those with cystic fibrosis (CF) is increasing due to the availability of new medications, rigorous care and prompt diagnosis of the disease.

The sweat gland defect in CF has been well characterized for years and is presently used to diagnose CF by the use of what is called the "pilocarpine iontophoresis sweat test."

Sweat production is stimulated through two pathways: the cholinergic pathway and by the adrenergic/sympathetic pathway (i.e., fight or flight response). Thus, sweat production can be stimulated by both cholinergic and adrenergic agonists. Collection of cholinergic stimulated sweat, using the cholinergic agonist pilocarpine, and the subsequent measurement of sweat chloride concentration is the basis of a standard diagnostic test for cystic fibrosis (CF), the pilocarpine iontophoresis sweat test. Stimulation of sweat production with pilocarpine leads to initial production of an isotonic secretion in the sweat gland. In non-CF patients, as the secretion traverses the sweat duct, chloride is reabsorbed. This leads to low concentration of chloride in sweat as it appears on the skin. This chloride resorption is dependent on the presence of functional CFTR. In CF patients, who lack functional CFTR, the sweat chloride concentration remains high, and distinguishes most, but not all, CF from non-CF patients. However, this technique does not distinguish heterozygote carriers of CFTR mutations from non-carriers, nor does the sweat chloride concentration correlate with disease severity. Furthermore, the pilocarpine iontophoresis sweat test involves the use of a sweat test apparatus consisting of electrodes and a voltage source and the use of specially trained personnel. These methods require the elution of the sweat electrolytes collected on the pads and determination of chloride content of the sweat. While this method remains the "gold standard", it occasionally yields ambiguous results. Therefore, it would be useful to have an alternative method of diagnosing CF.

As discussed above, sweat production is also stimulated by β-adrenergic agonists that lead to increases in intracellular cyclic AMP (cAMP) in the sweat duct epithelia. This response is dependent on the presence of functional CFTR, which is a cAMP-stimulated chloride transporter. It has been reported that CF subjects do not sweat after β-adrenergic stimulation. (Sato, K., et al., (1984), *J. Clin. Invest.*, 73:1763–1771.) It has also been reported that non-CF subjects have markedly increased sweat production rates compared to CF subjects, (Sato, K., et al. (1984), supra.; Sato, K., et al., (1988), *J. Lab. Clin. Med.*, 111:511–518) while non-affected carriers of a CFTR mutation have intermediate sweat rates. (Sato K. et al. (1988), supra; Behm et al., *Pediatric Research*, Vol. 22, No. 3 (1987), pp. 271–276). The rate of sweat production in response to β agonists is proportional to the number of functional copies of CFTR present in the subject's genotype.

It has also been reported that there are gender-related differences in cAMP-stimulated sweat rates due to sweat gland density, (Sato, et al, 1988 supra). Thus, it would be useful to have a method of determining sweat rates that is not gender-dependent.

The previously described method of measuring sweat rate in response to β-adrenergic stimulation is described in Sato, K., et al. (1984), supra.; and Sato K. et al. (1988), supra. Briefly, the method used by Sato, et al. involves the collection of beads of sweat secreted into an oil-filled sweat collection ring which is glued to the skin. The sweat collection chamber comprises a Teflon ring with a 7-mm hole in the center. This ring is glued to the skin of the forearm with contact cement. Paraffin oil, saturated with water, is poured into the trough of the chamber. A solution containing isoproterenol is injected into the dermis under the center of the test site. The sweat beads are collected using a glass capillary under a stereomicroscope. Sweat rates are calibrated by transferring the sweat sample into a constant bore calibration pipette. The procedure is depicted in Figure 2 of Sato, K., et al. (1984), supra. Sato determines the nanoliters of sweat produced over time, i.e., the sweat rate. See also Behm et al., *Pediatric Research*, Vol. 22, No. 3 (1987), pp. 271–276.

Other methods of measuring isoproterenol-stimulated sweat rate involve the use of a water vapor analyzer. Sato, et al, (1988) supra. β-adrenergic sweating is induced by injecting a solution containing isoproterenol to form an intradermal wheal. A capsule rim is coated with silicone grease, placed on the wheal and secured with tape. Dry nitrogen gas is introduced into the capsule and moisture in the outflow nitrogen gas is monitored by an electrolytic water vapor analyzer. The analyzer requires calibration and the leakage of nitrogen gas from the capsule-skin junction needs to be minimized.

The sweat rate of Sato is difficult to determine due to small amount of sweat that is produced. As a result, the sweat rate test is used in only a few CF centers and is not yet routinely recommended.

It would be useful to have the ability to quantitatively measure cAMP-induced sweat rates to improve the detection of CF patients and heterozygous CF carriers. It would also be useful to have a mechanism to study the effects of new and potentially useful systemic CFTR repair therapies for CF. It would especially be useful to have a mechanism to study systemic therapies that produce partial, rather than full, correction of the CFTR defect.

Presently used methods for stimulating sweat use pilocarpine iontophoresis and measure the amount of chloride produced in the sweat. These devices measure sweat produced by the cholinergic pathway, as is discussed above, and do not reliably distinguish between heterozygous carriers of the diseases and those who have CF.

It would be useful to have a method for measuring the amount of sweat produced by the β-adrenergic pathway that is less laborious and less technically demanding than the presently known methods.

SUMMARY OF THE INVENTION

The present invention relates to methods of diagnosing cystic fibrosis in a patient suspected of having the disease by measuring the cAMP mediated sweat secretion in response to β-adrenergic stimulation of the sweat glands. The present methods also enable the detection of heterozygous carriers of the disease.

More particularly, the present invention relates to a method of diagnosing CF comprising:

a) stimulating sweat production via β-adrenergic pathway, by increasing cAMP production;

b) collecting sweat into a sweat collection device;

c) determining the sweat rate as a function of the weight of the sweat collected;

d) correlating the sweat rate with the functional state of CFTR and/or presence or absence of CF.

Sweat production is stimulated by injecting into the patient a solution comprising an effective amount of at least one β agonist. Preferably the β agonist is selected from isoproterenol, albuterol, terbutaline and metaproterenol. In preferred embodiments, the β agonist comprises isoproterenol or compounds having similar effectiveness. The term "effective amount" refers to the amount necessary to increase cAMP production and increase sweat production in the subject.

In especially preferred methods, the solution further comprises a cAMP augmenting agent and an anticholinergic compound. The cAMP augmenting agent preferably decreases the breakdown of cAMP and is selected from methyl xanthines, such as theophylline and aminophylline, and milrinone or other similar compounds. The anticholinergic compound prevents interference from sweat produced by the cholinergic system. The anticholinergic compound is selected from known compounds, such as atropine, scopolamine, glycopyrrolate, ipratropium bromide (e.g., Atrovent) or others known in the art.

In a preferred embodiment, sweat production is stimulated by injecting a solution comprising isoproterenol, theophylline, and atropine.

In the present methods, the sweat rate is determined by absorbing the sweat onto a sweat collection device and weighing the device. The sweat collection device comprises any absorbant material such as paper or capillary coils. Preferably, it is filter paper. The sweat collection device preferably further comprises an airtight transport container. The collection device is carefully weighed prior to use. The absorbent material is placed over the area of the injection and preferably covered with an airtight barrier, such as plastic wrap and/or parafilm. Sweat is collected for a measured amount of time, ranging from 10–30 minutes, preferably about 20 minutes. The absorbent material is transferred to the airtight transport container and weighed on an analytical balance to determine the amount of sweat collected.

In other embodiments, sweat production through the cholinergic pathway is also stimulated at another test site. In such an embodiment, the sweat produced through the cholinergic pathway also collected into a sweat collection device and the sweat rate is determined, as described above. In these embodiments sweat is stimulated by injection of a cholinergic stimulating compound, e.g., methacholine (MCh), pilocarpine or other such compounds as are known in the art. This sweat rate can be used as a positive control, or as further described below, to normalize the results to compensate for gender-related differences in sweat rate.

The invention further relates to a method of screening compounds for diagnosis and/or treatment of cystic fibrosis. Such a method comprises: a) providing a compound of interest to a test subject; b) providing a composition to stimulate sweating by the β adrenergic pathway and collecting sweat into an absorption device; d) determining the sweat rate as a function of the weight of the sweat collected; e) correlating the sweat rate with the functional state of CFTR and/or the presence or absence of CFTR.

The order of stimulation may vary depending on the type of compound being tested. For example, steps a and b may be performed substantially at the same time. Alternatively, step b may be performed before step a. Another embodiment further comprises measuring sweat production between steps a and b.

The present invention also relates to kits for measuring the sweat rate in a patient suspected of having CF, comprising: a) a β-agonist, b) a cAMP augmenting agent, c) an anticholinergic compound; and d) sweat collecting device. The β-agonist, cAMP augmenting agent and anticholinergic compound may be combined in liquid form, or in powdered form. Alternatively, the kit comprises three different solutions or powdered compounds. In certain embodiments the kit further comprises a cholinergic stimulating compound, e.g., methacholine. The sweat collecting device preferably comprises a sweat absorbing material and an air-tight transport container. The kit may also contain an air-tight barrier comprising plastic and/or parafilm type material.

DETAILED DESCRIPTION OF THE INVENTION

The methods of the present invention enable the detection or diagnosis of cystic fibrosis in a fast and uncomplicated manner. The present methods do not require complicated machinery or highly skilled technicians. As used herein, the following terms are defined as follows:

The term "β-agonist" or "β-adrenergic agonist" refers to any compound that induces cAMP production in sweat glands, i.e., stimulates the β-adrenergic pathway of sweat production. Examples include isoproterenol, albuterol, terbutaline and metaproterenol.

The term "cAMP augmenting agent" refers to any compound that prevents or slows the breakdown of cAMP in sweat glands. Examples include: methyl xanthines, e.g., theophylline or aminophylline, and milrinone.

The term "anticholinergic compound" refers to any compound that inhibits the cholinergic pathway for the production of sweat. Examples include atropine, scopolamine, glycopyrrolate and ipratropium bromide (e.g., Atrovent).

In the preferred method of the present invention, sweat production is induced by the β-adrenergic pathway by introducing into a patient a solution containing a compound that increases cAMP production, e.g. a β-agonist. Preferably the solution is introduced by injection into the dermis, approximately 1 cm away from the site of measurement. Measurements can be taken at any location on the body where the sweat glands are easily accessible. A preferred site is the ventral forearm.

The solution is injected to raise a wheal, e.g., to resemble that of a standard intradermal PPD test for tuberculosis. The area of the wheal is covered with a sweat absorbing material, which is part of a sweat collection device. The sweat absorbing material comprises any type of absorbent material, such as filter paper, cotton wadding, capillary coils or other appropriate absorbent material known in the art. Preferably filter paper (e.g., Schleicher and Schuell, GB003) is used. Prior to application onto the skin of the patient, the sweat absorbing material is carefully weighed and tared using a standard laboratory analytical balance to about 0.1 mg. The precision of the measurement will depend on the tolerance of the scale, e.g., ±0.2–0.3 mg. The sweat absorbing material can be weighed separately, or together with an air tight transport container, which together comprise the sweat collection device. To prevent absorption of oils, moisture, etc. from the hands of the technician, gloves are worn and the absorbent device handled with forceps or other standard equipment. The area of the wheal is preferably washed with deionized water and alcohol and carefully dried prior to application of the sweat absorbing material.

To avoid the possibility of contamination of the sweat absorbing device with blood from the injection site, the absorbing device should be placed over the wheal in such away as to avoid the injection site. This is easily accomplished because the injection site is preferably about 1 cm from the site of the raised wheal.

The sweat absorbing material is covered by an airtight barrier, which prevents evaporation of the sweat from the material. Examples of airtight barriers include plastic, cellophane/plastic wrap, parafilm, and other materials known to be impervious to water and air. A combination of these materials may be utilized to maximize the amount of sweat absorbed by the device. In preferred methods plastic and parafilm is used. The plastic can be any type of flexible plastic, such as acetate, polyethylene, etc. In a preferred method, the sweat absorbing material, e.g., filter paper, which is placed on the site, e.g., the arm, is overlaid with plastic and parafilm is wrapped around the arm and pulled taut. The plastic is preferably larger than the sweat absorbing material. For example, the sweat absorbing material preferably has a size of from about 1 cm to about 4 cm in diameter, most preferably about 2.5 cm in diameter. The plastic is preferably larger than the sweat absorbing material. If the filter paper has a diameter of about 2.5 cm, the plastic may preferably be about 4 cm square. The parafilm or plastic wrap is larger than the plastic.

Sweat collection is allowed to proceed for a time that enables maximum sweat production. Because the response to β-agonists occurs quickly, maximum sweat production occurs within 10 minutes. Preferably sweat is collected within 30 minutes of the injection. More preferably, sweat is collected from about 5 minutes to about 30 minutes from the time of injection. Most preferably, sweat collection proceeds for about 20 minutes. At this point the airtight barrier is removed and the absorbing material is weighed. Preferably the absorbing material is placed in a tared, airtight container and then weighed.

The sweat rate is determined by dividing the amount of sweat collected, e.g., mg sweat, by the period of time for sweat collection, e.g., 20 minutes and is expressed as amount of sweat collected/time, e.g., mg/minute.

Preferred solutions for inducing sweat production comprise at least one β-agonist. Useful β-agonists are known and include any compound that increase cAMP production, resulting in increased sweat production in the patient. Examples for β-agonists include isoproterenol, albuterol, terbutaline and metaproterenol. Preferably, the β-agonist comprises isoproteronol. It may also be useful to use a combination of β-agonists.

In preferred methods of the present invention, the solution further comprises a cAMP augmenting agent and/or an anti-cholinergic compound. The cAMP augmenting agent is preferably selected from methyl xanthines, such as theophylline or aminophylline, and milrinone. Other compounds that prevent or decrease the breakdown of cAMP can be determined or selected by one of ordinary skill in the art. Preferred agents include theophylline and aminophylline.

Useful anti-cholinergic compounds include, e.g. atropine, scopolamine, ipratropium bromide and glycopyrrolate. These compounds block sweat production at the test site via the cholinergic system. Other compounds that prevent or decrease interference from sweat produced by the cholinergic system are known in the art. Preferably, the compound is atropine.

In a preferred method of the present invention, the injection solution comprises an effective amount of at least one β-agonist, a cAMP augmenting agent and an anticholinergic compound. Preferably the injection solution comprises isoproteronol, aminophylline and atropine.

The effective amount of each compound is determined based on known methods, e.g., Sato, et al., supra, and Behm, et al. supra. The injection solution may also comprise additives, buffers, etc., in a sterile solution, e.g. lactated Ringer's solution, as is known in the art.

The amounts of the compounds injected is typically significantly less than standard therapeutic doses given by more optimal routes. For example, the total amount of aminophylline ranges from about 0.5 to about 5.0 mg, preferably between 1–2 mg, which is significantly less than the standard adult infusion rate of 0.7–0.8 mg/kg/hour when used for status asthmatacus. The total isoproterenol dose will range from about 2 μg to about 15 μg, preferably between about 6–8 μg, which is significantly less than a standard infusion or nebulized dose (2 μg/kg/min or 0.5 mg respectively). Atropine dose ranges from about 1 μg to about 10 μg, preferably about 3–5 μg, which is significantly less than a standard dose of 0.02 mg/kg IV given for bradycardia or 1 mg given by nebulizer.

To increase precision and accuracy, the injections may be performed in duplicate, e.g., two injection sites in the dominant forearm.

In another preferred embodiment, the method further comprises injecting a cholinergic stimulating compound, e.g., methacholine (MCh) or pilocarpine, at another test site and measuring sweat rate. In such embodiments the total MCh dose ranges from about 0.005 mg to about 0.05 mg, preferably from about 0.01 mg to 0.03 mg, most preferably about 0.02 mg. This amount range is significantly less than the lowest aerosolized dose used for bronchial challenges, i.e., about 0.375 mg. In this embodiment, a third intradermal injection of a sterile solution of MCh, e.g. about 0.2 ml of 0.5 mM MCh in lactated Ringer's solution is performed. This injection stimulates sweat via the cholinergic pathway. Sweat is collected as describe above and the sweat rate calculated. This sweat rate is used to standardize for gender-related differences; e.g., due to sweat gland density. Normalization of the cAMP-stimulated sweat rate by MCh-stimulate sweat rate obviates the differences between males and females. See Sato, et al., 1988, supra.

In another embodiment, the sweat rate measured from the cholinergic agent, e.g., MCh, is used as a positive control.

That is, the cholinergic stimulating compound is injected into the subject separately, but having the same components of the injection as the β-adrenergic stimulating injection (less the β-agonist, anticholnergic compound and the cAMP augmenting agent).

The methods of the present invention include methods for determining whether a patient suffers from cystic fibrosis or is a carrier (i.e., is heterozygous) for the disease. If the methods described herein are performed on a patient suspected of suffering from CF and little, if any, sweat is collected, then the patient most likely has cystic fibrosis. If there is an increase in sweat production, the person most likely does not have cystic fibrosis. If a control test, e.g., consisting of injection of a cholinergic agent, e.g., MCh, is performed on the same patient, sweat should be collected. If sweat is produced by the β-agonist, but in an amount that is intermediate to a control subject (i.e., non-CF patient) and a CF patient, or intermediate to standard or norm values for non-CF subjects and CF-patients, then the subject is most likely a carrier of the disease (i.e., is heterozygous). If desired, other tests can be performed to confirm the diagnosis.

The present invention also relates to kits for diagnosing/detecting cystic fibrosis, or for selecting compounds useful in the treatment or diagnosis of cystic fibrosis. Such kits comprise a component for increasing cAMP and stimulating sweat production and a device for collecting sweat. The kit preferably combines a β-agonist, a cAMP augmenting agent and an anticholinergic compound as the component for stimulating sweat production. These may each be in solution or in powdered form, or be combined in solution or a powder. Certain kits will also include a cholinergic stimulating compound, in liquid or powdered form. Preferred kits comprise isoproterenol, theophylline (or aminophylline) and atropine. If a cholinergic compound is included, preferably, it comprises MCh.

As aforesaid, the kits include a sweat collecting device which comprises a sweat absorbing material. Preferred materials include filter paper, capillary coil, etc. The sweat collecting device preferably further comprises an air tight transport container. The container can be any type of container that can easily be opened and closed, is large enough for insertion of the sweat absorbing material and small enough to be easily weighed. Preferred containers are glass or plastic vials, e.g., Coulter counter or scintillation counter vials, with screw on or snap on tops. The kits may also include an air-tight barrier, e.g., plastic, and/or plastic wrap or parafilm. The sweat absorbing material and/or the plastic may be precut to the desired size, or cut from a sheet as needed.

The present invention also relates to methods of screening compounds for the diagnosis and/or treatment of cystic fibrosis. As described above, the absence of sweat production in response to β-adrenergic stimulation of the sweat gland in cystic fibrosis patients is due to the lack of functional CFTR. Thus, compounds that can compensate for the lack of functional CFTR or otherwise increase sweat production in cystic fibrosis patients could prove to be useful in the treatment of cystic fibrosis. The present invention provides a method for screening for such compounds. A test compound of interest is administered to a patient known to have cystic fibrosis (determined either by the methods of the present invention or other diagnostic methods) by any method known, i.e., orally, intravenously, by injection, topically or by inhalant. The test compound, i.e., drug, is administered locally or systemically according to the nature and type of drug. The sweat rate is then determined as previously described. That is, a solution is injected to stimulate sweating by the β-adrenergic pathway. Preferably, the solution contains isoproterenol, theophylline (or aminophylline) and atropine. The injection is administered to produce a wheal. A sweat absorption material, e.g. filter paper, is applied and covered with an airtight barrier to collect the sweat. The sweat absorbing material is weighed (preferably in an air-tight container) to determine the amount of sweat collected. The amount of sweat, i.e., the weight of the sweat, is used to determine the sweat rate. The sweat rate is calculated and related to the ability of the test compound of interest to stimulate CFTR function in the sweat gland and allow sweat production after cAMP stimulation in a patient suffering from cystic fibrosis. In other words, if the sweat rate increases after administration of the test compound, that test compound may prove useful in treating CF.

The order of the above steps can vary depending on the type of compound to be tested. For example, it may be desirable to introduce the test compound of interest at eventually the same time as the β-adrenergic stimulating solution. Or the test compound of interest may be administered prior or subsequent to the stimulating solution.

It may also be desirable to determine and compare the sweat rate before and after administration of the test compound and the stimulating solution.

If the compound of interest is administered over a period of time, the sweat rate is measured during the time course of treatment. If the sweat rate increases during the treatment, the test compound may be useful drug for therapy.

In particular embodiments, the method of diagnosing and/or detecting cystic fibrosis is gender-specific. This method further comprises comparing the sweat rate obtained with a gender-specific norm or standard. The gender-specific norms or standards can be determined by one of ordinary skill in the art after evaluation of a statistically significant number of subjects, e.g., about 20 patients of each gender in each of the three groups (control, carrier/heterozygote, and CF patients).

The present invention is further illustrated by the following examples, which are provided to aid in the understanding of the invention and are not construed as a limitation thereof.

EXAMPLE 1

Aseptic conditions are maintained throughout the protocol.

Two sites on the ventral forearm were cleaned with alcohol wipes and allowed to dry. 0.3 ml of a sterile solution of 50 $\mu$M Isoproterenol, 5 mM Aminophylline, and 140 $\mu$M Atropine sulfate (to block cholinergic sweat simulation at the site of the adrenergic sweat stimulation) in Lactated Ringer's was injected intradermally to raise a wheal. The wheal resembled that of a standard intradermal PPD test for tuberculosis.

The area of the wheal was overlaid with carefully tared filter paper. To minimize the possibility of contamination of the filter paper for sweat collection with blood from the injection site, the actual skin puncture was about 1 cm from the site of the raised wheal and the filter paper was not placed over the injection site. The filter paper was covered with an airtight barrier (plastic and parafilm) and sweat collection proceeded for 20 minutes. The filter paper was then weighed in a tared, airtight container to ascertain the mass of sweat collected.

A third intradermal injection of a sterile solution of 0.2 ml of 0.5 mM methacholine in Lactated Ringer's was used to stimulate sweat via the cholinergic pathway.

Adrenergic-stimulated sweat rate was expressed as mg sweat collected/20 min, and the individual rates from each arm were averaged prior to data analysis.

The ISO-induced sweat rates (in mg sweat per 20 minutes, expressed as mean ±SEM) were the following:

CF patients 1.2±0.22 (n=19)

Heterozygotes 2.5±0.22 (n=22)

Controls 3.8±0.47 (n=21)

Differences between CF patients and Heterozygotes (p=0.023), Heterozygotes and Controls (p=0.017) and CF patients and Controls (p<0.001) were statistically significant by one-way ANOVA using Bonferroni's adjustment for multiple comparisons. The means ±SEM of methacholine-induced sweat rates did not significantly differ between groups (CF patients, 36±5.4; Heterozygotes, 27±3.4; Controls, 37±4.3; p>0.480 for all comparisons among groups).

EXAMPLE 2

There are gender-related differences in cAMP-stimulated sweat rates due to sweat gland density (Sato, et al. (1988)). Thus, a third intradermal injection of a sterile solution of 0.2 ml of 0.5 mM methacholine in Lactated Ringer's was used to stimulate sweat via the cholinergic pathway. The sweat was collected and the cAMP-stimulated sweat rate was normalized by the methacholine stimulated sweat rate. In previous experiments, this normalization obviated the differences in sweat rate between males and females (Sato, et al. (1988)).

This protocol was performed on 46 individuals (15 subjects with CF, 16 obligate heterozygotes, and 15 controls). The means ±SEM cAMP-stimulated sweat rates normalized by methacholine sweat rates (expressed as %) in the groups were:

CF patients 4.85±1.13

Heterozygotes 11.51±1.34

Controls 12.89±1.03.

Statistical analysis was preformed by one-way ANOVA (analysis of variance). Zar, J. H., (1984) Biostatistical Analysis, Prentice-Hall, Inc., Englewood Cliffs, N.J. There was a highly significant difference between CF and Control (p<0.001) and CF and Heterozygotes (p=0.001).

EXAMPLE 3

An alternative means of obviating the difference in sweat rates between males and females is the determination of gender-specific norms for cAMP-stimulated sweat rate without normalization for methacholine. This procedure provided a more reproducible measure and better demonstrated the hypothesized linear relationship between amount of CFTR function and cAMP-stimulated sweat rate. The data presented below for females and males shows cAMP-stimulated sweat rates.

For females, a total of 33 subjects were tested (7 CF, 14 heterozygotes, 12 controls). The mean ±SEM for the cAMP-stimulated sweat rate (expressed as mg sweat/20 min sweat collection) are:

CF patients 1.56±0.26

Heterozygotes 2.22±0.23

Controls 3.50±0.68.

Within this emerging trend, there is a statistically significant difference between CF females and control females (p=0.041).

In males, 16 subjects have been tested (8 CF, 4 Heterozygotes, 4 Controls). The mean ±SEM for the cAMP-stimulated sweat rate (expressed as mg sweat/20 min sweat collection) for males are:

CF patients 0.89±0.35

Heterozygotes 3.23±0.65

Controls 5.24±1.34.

Within this emerging trend, there is a statistically significant difference between CF males and control males (p=0.002). The difference between CF males and heterozygous males is approaching statistical significance (p=0.096 currently).

To correct for non-specific absorption of skin surface substances and unstimulated sweat, a "sham" sweat collection can be performed where the filter paper is placed for 20 minutes over an uninjected skin site, but otherwise handled in exactly the same manner as the cAMP-stimulated collection.

EXAMPLE 4

A subgroup of 11 patents was tested serially at weekly intervals. These tests demonstrated high intrapatient correlation coefficients (±SD) of 0.71 for cAMP stimulated sweat rates and 0.91 (±0.03) for methacholine stimulated sweat rates. The data show that the method of the invention is consistent and reproducible over a number of weeks. These data suggest that this cAMP-stimulated sweat test is useful as a quantitative measure of CFTR function in the sweat gland, both diagnostically and as a surrogate outcome measure during development of therapeutics.

EXAMPLE 5

To test a compound for usefulness as a drug therapy for treatment of CF, an initial sweat rate is performed according to the methods of Example 1. A test compound of interest is administered to the CF patient. During the course of treatment, the sweat rate is measured, as taught herein. If the sweat rate increases over the time course of treatment, then the test compound may prove to be useful for treatment of CF.

All documents mentioned herein are incorporated herein by reference in their entirety.

The invention has been described in detail with particular reference to the preferred embodiments thereof. However, it will be appreciated that modifications and improvements within the spirit and teachings of the inventions may be made by those in the art upon considering the present disclosure.

What is claimed is:

1. A method of diagnosing cystic fibrosis in a patient comprising
   a) stimulating sweat production via β-adrenergic pathway;
   b) collecting sweat into a sweat collection device for a predetermined amount of time;
   c) determining the sweat rate as a function of the weight of the sweat collected;
   d) correlating the sweat rate with the functional state of cystic fibrosis transmembrane conductance regulator and/or the presence or absence of cystic fibrosis.

2. The method according to claim 1, wherein the step of stimulating sweat production comprises injecting into the patient a solution comprising at least one β agonist.

3. The method according to claim 2, wherein the β agonist is selected from isoproterenol, albuterol, terbutaline and metaproterenol.

4. The method according to claim 2, wherein the solution further comprises a cAMP augmenting agent and an anticholinergic compound.

5. The method according to claim 4, wherein the cAMP augmenting agent is selected theophylline, aminophylline, and milrinone and the anticholinergic compound is selected from atropine, scopolamine, glycopyrrolate or ipratropium bromide.

6. The method according to claim 5, wherein the cAMP augmenting agent is theophylline or aminophylline and the anticholinergic compound is atropine.

7. The method according to claim 4, wherein the solution comprises isoproterenol, theophylline, and atropine.

8. The method according to claim 1, wherein the step of collecting sweat into a sweat collection device comprises absorbing sweat onto a sweat absorbing material.

9. The method according to claim 8, wherein the step of collecting sweat further comprises placing the sweat absorbing material into an air-tight transport container.

10. The method according to claim 1, wherein the step of determining the sweat rate comprises weighing the sweat collection device and dividing the amount of sweat by the time of collection.

11. The method according to claim 1, further comprising stimulating sweat production through the cholinergic pathway; collecting sweat into a sweat collection device; and determining the sweat rate as a function of the weight of the sweat collected.

12. A method of screening compounds for treatment of cystic fibrosis, comprising:

a) providing a compound of interest to a test subject;

b) providing a composition to stimulate sweat production by the β-adrenergic pathway;

c) collecting sweat onto a sweat absorbing material; and d) determining the sweat rate as a function of the weight of the sweat collected;

e) correlating the sweat rate with the functional state of cystic fibrosis transmembrane conductance regulator and/or presence or absence of cystic fibrosis.

13. A kit for measuring the sweat rate in a patient suspected of having cystic fibrosis, comprising:

a) a composition to stimulate sweat production via the β-adrenergic pathway;

b) sweat absorbing material;

c) air-tight transport container; and d) air-tight barrier.

14. The kit according to claim 13, wherein the composition to stimulate sweat productions comprises a β-agonist, a cAMP augmenting agent and an anti-cholinergic compound.

15. The kit according to claim 14, wherein the composition comprises isoproterenol, aminophylline and atropine.

16. The kit according to claim 13, further comprising methacholine.

17. The method according to claim 4, wherein the cAMP augmenting agent is methyl xanthine.

* * * * *

UNITED STATES PATENT AND TRADEMARK OFFICE
CERTIFICATE OF CORRECTION

PATENT NO. : 5,976,499

DATED: November 2, 1999

INVENTOR(S): Ronald Craig Rubenstein and Pamela Leslie Zeitlin

It is certified that errors appear in the above-identified patent and that said Letters Patent is hereby corrected as shown below:

Column 1, Line 4, after the Title of the Invention, please insert:

-- STATEMENT OF GOVERNMENT SUPPORT

Funding for this invention was provided in part by the Government of the United States of America through Contract Nos. RUBENS96LO, ZEITL196PO and ZEITL197AO from the Cystic Fibrosis Foundation and Contract Nos. PO1 HL51811 and RO1 HL47122 from NIH/NHLBI. The Government has certain rights in this invention.--

Signed and Sealed this

Third Day of April, 2001

Attest:

NICHOLAS P. GODICI

*Attesting Officer*   *Acting Director of the United States Patent and Trademark Office*